US008273307B2

(12) United States Patent
Eickhoff et al.

(10) Patent No.: US 8,273,307 B2
(45) Date of Patent: Sep. 25, 2012

(54) MICRODISPENSER AND ASSOCIATED OPERATING METHOD

(75) Inventors: Holger Eickhoff, Syke (DE); Christian Wurzel, Berlin (DE)

(73) Assignee: Scienion AG, Berlin (DE)

( * ) Notice: Subject to any disclaimer, the term of this patent is extended or adjusted under 35 U.S.C. 154(b) by 726 days.

(21) Appl. No.: 11/720,265

(22) PCT Filed: May 29, 2006

(86) PCT No.: PCT/EP2006/005114
§ 371 (c)(1),
(2), (4) Date: Jun. 21, 2007

(87) PCT Pub. No.: WO2006/128662
PCT Pub. Date: Dec. 7, 2006

(65) Prior Publication Data
US 2009/0060793 A1   Mar. 5, 2009

(30) Foreign Application Priority Data

Jun. 3, 2005 (DE) .................. 10 2005 025 640

(51) Int. Cl.
*B01L 3/02* (2006.01)
(52) U.S. Cl. ........ 422/501; 422/504; 422/507; 422/516; 422/520; 422/521; 73/863.32; 73/864; 73/864.01; 73/864.02; 73/864.11; 73/864.13
(58) Field of Classification Search ................. 422/100, 422/500–501, 504, 508–509, 511, 513, 516, 422/518, 520–525, 527, 537; 73/863.32, 73/864, 864.01, 864.03, 864.11, 864.15
See application file for complete search history.

(56) References Cited

U.S. PATENT DOCUMENTS

| 2,692,503 | A | * | 10/1954 | Crecelius ................... 73/864.03 |
| 4,162,030 | A | | 7/1979 | Capra et al. |
| RE30,845 | E | * | 1/1982 | Ossona de Mendez et al. .............. 356/440 |
| 4,418,354 | A | | 11/1983 | Perduijn |
| 4,484,696 | A | * | 11/1984 | Bajard ............................ 222/64 |
| 4,528,578 | A | | 7/1985 | Balbo |
| 4,528,579 | A | | 7/1985 | Brescia |
| 5,338,688 | A | | 8/1994 | Deeg et al. |
| 5,447,864 | A | | 9/1995 | Raybuck et al. |

(Continued)

FOREIGN PATENT DOCUMENTS

DE 2653051 A1 5/1978

(Continued)

OTHER PUBLICATIONS

Wehl, "Akustik und Fluidmechanik in Kanalen und Dusen von Tintenschreibwerken", Technical University of Munich (1984), pp. 1-78.

(Continued)

*Primary Examiner* — Brian R Gordon
(74) *Attorney, Agent, or Firm* — Caesar, Rivise, Bernstein, Cohen & Pokotilow, Ltd.

(57) ABSTRACT

The invention relates to a microdispenser (1) for dispensing a liquid sample in a dispensing device, with a sample container (2) for receiving the liquid sample, and with a nozzle (7) for dispensing the sample located in the sample container (2). The microdispenser (1) with the filled sample container (2) can in this case be stored independently of and fluidically separately from the dispensing device, without the sample escaping from the sample container (2) during storage.

32 Claims, 10 Drawing Sheets

U.S. PATENT DOCUMENTS

| | | | |
|---|---|---|---|
| 5,650,506 A | 7/1997 | Woodard et al. | |
| 5,705,628 A | 1/1998 | Hawkins | |
| 5,736,105 A * | 4/1998 | Astle | 422/100 |
| 5,891,087 A * | 4/1999 | Ohtani et al. | 604/89 |
| 5,898,071 A | 4/1999 | Hawkins | |
| 6,001,309 A * | 12/1999 | Gamble et al. | 422/507 |
| 6,037,465 A | 3/2000 | Hillebrand et al. | |
| 6,101,946 A | 8/2000 | Martinsky | |
| 6,110,363 A | 8/2000 | Hillebrand et al. | |
| 6,232,129 B1 | 5/2001 | Wiktor | |
| 6,296,811 B1 | 10/2001 | Sasaki | |
| 6,343,717 B1 | 2/2002 | Zhang et al. | |
| 6,401,769 B1 | 6/2002 | Backes et al. | |
| 6,457,612 B1 | 10/2002 | Zhang et al. | |
| 6,554,792 B2 * | 4/2003 | Hughes | 604/85 |
| 6,599,479 B1 * | 7/2003 | Kietzmann et al. | 422/502 |
| 6,852,851 B1 | 2/2005 | Tooke et al. | |
| 6,866,825 B2 | 3/2005 | Chiou et al. | |
| 7,927,618 B2 * | 4/2011 | Bodmeier | 424/423 |
| 2002/0064482 A1 * | 5/2002 | Tisone et al. | 422/100 |
| 2002/0113850 A1 * | 8/2002 | Wheeler et al. | 347/85 |
| 2002/0164808 A1 * | 11/2002 | Itaya et al. | 436/54 |
| 2003/0007897 A1 * | 1/2003 | Creasey | 422/100 |
| 2003/0190263 A1 * | 10/2003 | Yiu | 422/100 |
| 2006/0128024 A1 * | 6/2006 | Plank | 436/56 |
| 2007/0178016 A1 * | 8/2007 | Jost | 422/100 |
| 2011/0220239 A1 * | 9/2011 | Reed et al. | 141/1 |

FOREIGN PATENT DOCUMENTS

| | | |
|---|---|---|
| DE | 4447015 A1 | 7/1996 |
| DE | 10106362 A1 | 9/2002 |
| EP | 0469444 A1 | 2/1992 |
| EP | 0880535 B1 | 9/2003 |
| WO | 9721090 A1 | 6/1997 |
| WO | 9744134 A1 | 11/1997 |
| WO | 9930168 A1 | 6/1999 |
| WO | 0242175 A1 | 5/2002 |
| WO | 2004099059 A2 | 11/2004 |

OTHER PUBLICATIONS

International Search Report for PCT/EP2006/005114.

* cited by examiner

MICRODISPENSER AND ASSOCIATED OPERATING METHOD

BACKGROUND OF THE INVENTION

The invention relates to a microdispenser for dispensing a liquid sample in a dispensing device and also to an associated operating method.

Microdispensers are known for example from WO 99/30168 and are used inter alia for biological or chemical purposes in order to dispense small volumes of liquid in a controlled manner in the form of microdroplets. One example of this is the production of miniaturized DNA arrays for genetic engineering uses, wherein a high clone density is achieved by means of a small droplet size, for which piezoelectrically operated microdispensers are particularly suitable. The known microdispensers consist of a glass capillary for holding the sample liquid to be dispensed, the glass capillary having a nozzle for dispensing the microdroplets and a flexible supply line for filling it with the sample liquid. The discharging of the microdroplets from the glass capillary in the known microdispensers is brought about by means of a piezo actuator, which surrounds the glass capillary in the manner of a sleeve in the region of a narrowing and expands or compresses the glass capillary in the radial and/or longitudinal direction in the event of electrical actuation, as a result of which a shock wave is generated in the glass capillary which, after reflection at the narrowing of the glass capillary, discharges microdroplets out of the glass capillary through the nozzle.

One disadvantage of the known microdispensers described above is the fact that filling and operation of the glass capillary via a flexible hose can lead to contamination since the plastic hoses which are typically used, may form biofilms. Sterile handling of the transition points between the plastic hose and the glass capillary is particularly problematic, since this area contains corners and edges in which it is possible for contaminations (e.g. biofilms) to be deposited, in which bacteria, viruses, fungi and yeasts may in turn settle. This problem of contamination when filling the glass capillaries is particularly disadvantageous when the microdispensers are used in the diagnostics sector, since the contamination may then lead to faulty products and incorrect diagnoses.

When handling the known microdispensers, the problem generally exists that the microdispensers are subjected to operating cycles which consist of uptake by suction (filling), dispensing and subsequent rinsing. These operating cycles are repeated with the same microdispenser for the next sample or for a number of samples and may lead to so-called cross-contamination, and take up a large amount of time.

Furthermore, it must be noted with regard to the prior art that, in the case of so-called high throughput screening, the substances to be tested are usually stored dissolved in DMSO (dimethyl sulphoxide) in microtiter plates, wherein the microtiter plates containing a plurality of samples are deep-frozen. In order to remove a single sample, the entire microtiter plate along with all the samples located therein then has to be thawed, whereby moisture from the air can condense into the samples, which leads to impairment of the samples.

Furthermore, U.S. Pat. No. 6,191,946 discloses a microdispenser which is filled, cleaned and emptied via the nozzle. Moreover, the microdispenser in this case has a sample channel which is accessible from outside and therefore cannot be stored or transported in the filled state.

WO 97/44 134 A1 also discloses a microdispenser, which is filled from the front via the nozzle and therefore has the same problems as the known microdispenser described above, i.e. the microdispenser cannot be stored or transported in the filled state.

Patent application EP 0 469 444 A1 discloses a disposable (single-use) nozzle unit which contains the analysis liquid in pre-filled form. However, here the analysis liquid is discharged according to the bubble-jet technique, which heats up the analysis liquid and therefore is not suitable for the microdispenser according to the invention since, with the small dimensions of the microdispenser according to the invention, the heating that is required in the bubble-jet method in order to produce vapor bubbles would damage, i.e. denaturize, the biological samples in the sample liquid.

U.S. Pat. No. 6,296,811 B1 and U.S. Pat. No. 6,866,825 disclose a microdispenser in which the filling of the microdispenser with the sample liquid to be dispensed takes place via lines, which is associated with the problems of contamination described above.

Furthermore, DE 26 53 051 A1 and DE 101 06 362 A1 disclose pipettes for taking blood, which also allow storage. However, these are not microdispensers within the meaning according to the invention. The same applies in respect of the pre-filled pipettes known from WO 02/42175 A1 and U.S. Pat. No. 6,457,612.

Moreover, U.S. Pat. No. 6,232,129 B1 discloses a conventional piezoelectric pipetting device for transferring droplets of samples between two containers. However, these pipetting devices do not allow long-term storage in the filled state.

Finally, U.S. Pat. No. 4,528,579, U.S. Pat. No. 4,418,354 and U.S. Pat. No. 4,528,578 disclose microdispensers for inkjet printers, which as such are not suitable for dispensing biological samples.

The task of the invention is therefore to improve the known microdispensers in such a way that as far as possible no contamination or impurities occur.

SUMMARY OF THE INVENTION

This task is solved by a microdispenser according to the invention and by an associated operating method.

The invention encompasses the general technical teaching of using a microdispenser not only for dispensing purposes but also for storing and transporting the sample that is to be dispensed, so that there is no need to fill the microdispenser at the start of a dispensing operation, as a result of which the problems of contamination which occur in the prior art can be avoided. Furthermore, no time-intensive rinsing operations are carried out.

The microdispenser according to the invention can therefore be stored and/or transported with the filled sample container independently of and fluidically separated from the actual dispensing device, without the sample liquid escaping from the sample container during storage or during transport. The known microdispensers described in the introduction are not suitable for this, as will be discussed below. In the known microdispensers with a flexible supply line for filling the sample container, the sample liquid could escape via the flexible supply line during storage or during transport. By contrast, in the other known microdispensers in which filling takes place from the front via the nozzle, the filling via the nozzles and the subsequent closing of the nozzles would take up a large amount of time.

The microdispenser according to the invention is preferably also characterized in that the filling of the sample container with the sample liquid takes place separately from the dispensing operation, whereas the filling operation in the case of the known microdispensers using a flexible supply line takes place immediately before or during the dispensing operation. In practice, the sample container of the microdispenser according to the invention is usually filled prior to the dispensing operation, whereas no refilling is provided during the subsequent dispensing operation.

In one variant of the invention, the microdispenser is configured for single use, wherein the sample container (e.g. a glass capillary) is not refillable. In this variant, the single-use microdispenser is filled with the desired sample liquid at the factory and then stored and delivered, i.e. transported to the customer, in the filled state, wherein no sample liquid can escape from the microdispenser. In this way, contamination of the sample liquid located in the microdispenser is completely prevented, since the sample liquid is enclosed in the microdispenser in a sterile manner. Preferably, the sample container is therefore fully closed apart from the nozzle and, apart from the nozzle which is closed during storage or transport, has no other opening through which sample liquid could escape during storage or transport.

On the other hand, in another variant of the invention, the microdispenser has a valve for venting the sample container during the dispensing operation and/or for filling the sample container, which allows reuse of the microdispenser according to the invention. The microdispenser can, e.g., be filled with the desired sample liquid through the valve at the factory, and then the valve is closed during storage and transport. For the actual dispensing operation, the valve is then opened in order to vent the sample container, so that the dispensing of the sample is not prevented due to the build-up of an excess vacuum within the sample container. The valve in this case is preferably structurally integrated in the microdispenser and forms a unit with the microdispenser, whereby the dispenser according to the invention differs from the known microdispensers described above in which a supply line is connected to a separate pressure control device.

Within the context of the invention, single use means that the microdispenser is filled with the sample substance once, i.e. usually at the factory. Once this filling has been dispensed, the dispenser is disposed of. Reusable in the present context means that the microdispenser can be used one or more times in the dispensing device. Between the individual dispensing operations, the microdispenser is stored along with the sample contained therein.

The microdispenser according to the invention preferably has a marking which contains information about the microdispenser and/or the sample located in the sample container. This is particularly useful when the microdispenser is filled at the factory and then is delivered in the filled state, since the end user can then identify the sample located in the sample container on the basis of the marking, as a result of which incorrect use is avoided.

The marking for identifying the microdispenser and/or the sample may for example consist of an optical code, such as e.g. a one-dimensional or two-dimensional barcode which is optically read. However, it is also possible as an alternative that the microdispenser according to the invention has an integrated transponder which can be read in a wireless manner, which allows a high degree of automation. In one particular embodiment of the microdispenser according to the invention, the latter is equipped with a transponder which has both a "read-only" area and a "read and write" area. In this embodiment, the tracking of the sample is solved for example in a particularly advantageous manner since each storage operation and each dispensing operation is stored directly on the microdispenser itself, for example along with a date stamp, the number of dispensed droplets or the batch number of the array produced.

In the microdispenser according to the invention, a sponge located in the sample container may for example be used to prevent the sample liquid from escaping from the sample container through the nozzle, in that the sponge exerts on the sample liquid a capillary force, which generates a holding vacuum in the sample container. The holding vacuum in the microdispenser according to the invention may be between 1 mbar and 100 mbar, but the invention is not restricted to this range of values with regard to the holding vacuum.

However, it is also possible as an alternative that the nozzle is closed for transport and/or storage, by means of a stopper, a film, by means of wax or by means of a closure cap.

Preferably, the sample container (e.g. a glass capillary) in the microdispenser according to the invention has a stepped cross section at which shock waves are reflected, said shock waves being generated by an actuator (e.g. a conventional piezo actuator). In one variant of the invention, the stepped cross section consists of a narrowing of the cross section, as is known from the prior art. By contrast, in another variant of the invention, the stepped cross section consists of a widening of the cross section, which also leads to the reflection of shock waves in the region of the stepped cross section. With regard to the configuration of the stepped cross section in order to achieve the desired reflection effect, reference should be made to Wolfgang Wehl: "Akustik und Fluidmechanik in Kanälen und Düsen von Tintenschreibwerken", Dissertation TU Munich, 2nd edition 2002, the content of which is hereby fully incorporated in the present description, so that there is no need at this point for a detailed description of the configuration of the stepped cross section.

The sample container and/or the nozzle in the microdispenser according to the invention may be made for example of plastic, glass or ceramic, but the invention is not restricted to the aforementioned materials with regard to the materials for the sample container and/or the nozzle, but rather in principle it is also possible for these to be made of other materials.

Preferably, however, the sample container and/or the nozzle in the microdispenser according to the invention consist of an inert material, such as glass for example.

Furthermore, the microdispenser according to the invention preferably has an actuator for discharging the sample located in the sample container, wherein the actuator is preferably structurally integrated in the microdispenser.

However, it is also possible as an alternative that the actuator is structurally separate from the microdispenser and the latter is brought together with the actuator only at the time of the dispensing operation. The microdispenser according to the invention can therefore be stored and transported without the actuator.

By way of example, the actuator can be connected to the sample container by means of a material fit, friction fit and/or form fit.

Preferably, the actuator surrounds the sample container in the manner of a sleeve, as known per se from the prior art. Here, the sleeve-like actuator can be pushed onto the sample container, wherein the actuator can be fixed in the pushed-on state by means of a mounting sleeve. The mounting sleeve may for example be fixed on the sample container by screwing or by means of a securing ring. It is also advantageous if the mounting sleeve has a spring slot which runs in the axial direction, so that the mounting sleeve can expand slightly in the radial direction.

Furthermore, it is advantageous if the nozzle and/or the sample container is provided with a coating which acts in a protein-immobilizing or DNA-immobilizing manner. Such coatings are described for example in EP 0 880 535 B1, DE 44 470 15 A1, U.S. Pat. No. 6,852,851, U.S. Pat. No. 5,650,506, U.S. Pat. No. 5,705,628, U.S. Pat. No. 5,898,071, U.S. Pat. No. 5,447,864 and WO 97/21090, so that the content of these publications is hereby fully incorporated in the present description with regard to the structure and composition of the immobilizing coating.

It is also advantageous if the nozzle and/or the sample container is provided with a coating which permits specific adsorption of biomolecules, prevents coagulation of a sample contained in the microdispenser and/or is suitable for purifying and/or concentrating the sample. Suitable substances for such coatings are known per se from standard methods of biotechnology and biochemistry.

It should also be mentioned that the sample container preferably has a volume in the range from 1 nl to 1 ml, while the nozzle preferably has a nozzle diameter in the range from 10 µm to 100 µm. However, the invention is not restricted to the aforementioned ranges of values with regard to the volume of the sample container and the nozzle diameter, but rather can in principle also be implemented with other values.

Furthermore, the sample container preferably has both a sample reservoir and a working chamber. The working chamber in this case serves to discharge an individual sample from the microdispenser. To this end, the working chamber can be compressed radially and/or longitudinally for example by means of a piezo actuator, as known per se. The sample reservoir, on the other hand, serves to hold a sufficient quantity of sample to make it possible to dispense a number of samples one after the other without having to refill the microdispenser in a manner that may lead to contamination. The sample reservoir therefore preferably has a larger volume than the working chamber of the sample container.

In one variant of the invention, the nozzle consists only of a suitably shaped nozzle opening of the sample container. However, it is also possible as an alternative that the nozzle is formed by a separate nozzle film, a nozzle cap or a nozzle stopper, which close an opening in the sample container.

Furthermore, it is also possible within the scope of the invention that the sample reservoir permits a change in volume on account of the design or the material used. The sample reservoir may for example have a flexible and preferably elastic wall, so that the volume of the sample reservoir can be reduced by compressing the sample container in the region of the sample reservoir.

The sample reservoir may for example also be formed by an elastic membrane or a flexible hose. The change in volume in this case can take place for example by applying an external fluidic pressure to the membrane or the hose. Alternatively, it is possible that the volume of the sample reservoir can be changed by pressing a ram against the membrane or onto the hose. In the case of a hose, another possibility for reducing the volume consists in rolling up or folding the hose.

It is also possible that the sample reservoir consists of a tube in which a ram can be displaced, so that the position of the ram within the tube determines the volume of the sample reservoir. The ram may in this case be an integral part of the sample container or else can be moved by applying an external force (e.g. pressure, lever).

It should also be mentioned that the sample reservoir preferably has a flexible wall so that, when a sample is dispensed, the volume of the sample reservoir can be adapted according to the dispensed volume of sample.

Furthermore, the invention is not restricted to the above-described microdispenser according to the invention as an individual part, but rather also encompasses a complete dispensing device comprising at least one microdispenser according to the invention. Here, the dispensing device may be characterized in that no sample supply line for the microdispenser is provided, so that the microdispenser is fluidically separated from the dispensing device. The dispensing device in this case merely brings about actuation of the associated actuator for dispensing droplets, and in some circumstances also the spatial positioning and orientation of the microdispenser.

The microdispenser according to the invention is particularly advantageous for producing so-called working copies for screening processes in the pharmaceutical industry for example. This relates for example to the production of so-called microarrays or to the production of multiple assays. In the working methods of the prior art, aliquots are taken from the substances, which are generally located in microtiter plates or other containers, and these aliquots are distributed in microtiter plates. From these so-called grandmother plates, mother and then daughter plates (copies) are produced by means of two further aliquot-taking and multiplication steps. To this end, the microtiter plates which have been filled with the sample substances and deep-frozen firstly have to be thawed in order to allow removal of the liquid sample substances. During this thawing operation, moisture from the air may condense into the sample substances, which leads to impairment of the sample substances as has already been mentioned above. After thawing, the sample substances are then removed from the respective mother plate and transferred to a so-called daughter plate. In the same way, a further copy is then created from the daughter plate, this further copy being referred to as the screening plate or microarray. This procedure, which corresponds to the prior art, is difficult and complicated and consists of a large number of individual steps which may lead to contamination, cross-contamination, delays, dilution errors or dilution due to condensing water. Moreover, an individual sample can be taken only by carrying out the process on the entire microtiter plate. By contrast, the microdispenser according to the invention is particularly suitable for producing working copies in the screening process in the form of microarrays, multiple assays or for producing so-called diagnostic chips. Here, the sample substance is filled directly from the grandmother plate into the microdispenser and used to produce for example the arrays. There is no need for the mother and daughter plates which would otherwise be necessary. Individual samples can be dispensed without having to thaw the entire microtiter plate. It should also be mentioned that the invention is not restricted to the microdispenser described above and to a corresponding dispensing device, but rather also encompasses a corresponding operating method as will already be obvious from the above description.

The microdispenser according to the invention may be handled manually in the conventional manner by an operator.

However, it is also possible as an alternative that the microdispenser according to the invention may be handled by a robot. The microdispenser according to the invention is therefore preferably compatible, in terms of its dimensions and shape, with conventional robots for handling microdispensers, so that the microdispenser according to the invention can also be handled by conventional robots without any structural adaptations to the robots being necessary.

BRIEF DESCRIPTION OF SEVERAL VIEWS OF THE DRAWINGS

Other advantageous further developments of the invention are characterized in more detail below with reference to the figures, together with the description of the preferred examples of embodiments. In the figures:—

DETAILED DESCRIPTION OF PREFERRED EMBODIMENTS

Figure 1:
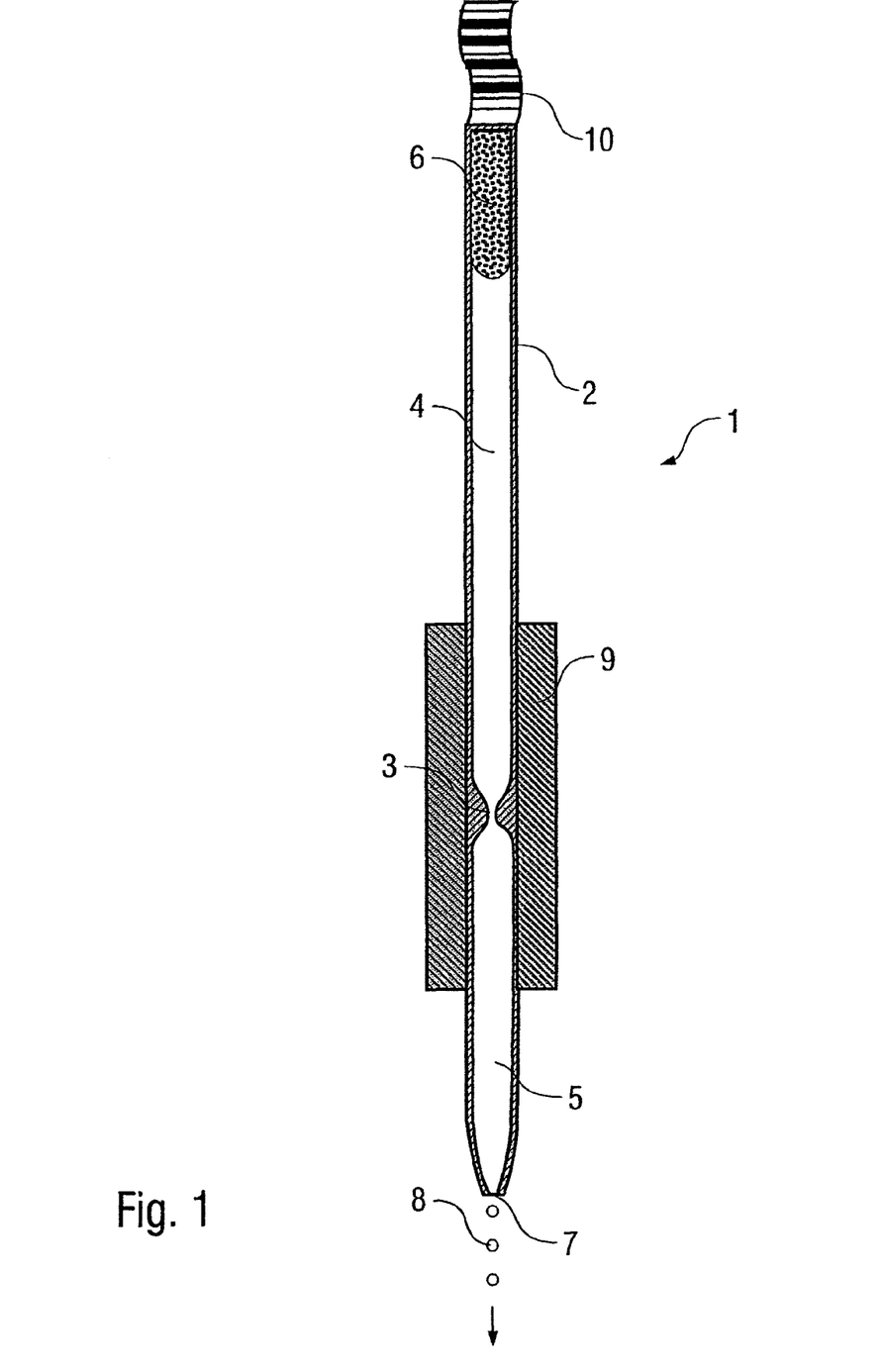
FIG. 1 shows a cross-sectional view of a single-use microdispenser according to the invention.

The cross-sectional view in FIG. 1 shows a microdispenser 1 according to the invention which can be used in a dispensing device (not shown) to dispense microdroplets.

In order to hold a sample liquid, the microdispenser 1 has a sample container 2 in the form of a glass capillary with a volume of 20 µl, wherein the sample container 1 has a narrowing 3 which divides the sample container 2 into a sample reservoir 4 and a working chamber 5.

Arranged in the sample reservoir 4 is a sponge 6 which exerts on the sample liquid capillary forces which generate a holding vacuum in the sample reservoir 4, as a result of which the sample liquid is prevented from running out of the sample container 2.

Furthermore, the sample container 2 has a nozzle 7 with a nozzle diameter of 70 µm, through which microdroplets 8 can be dispensed.

The dispensing of the microdroplets 8 is brought about by a piezo actuator 9 which surrounds the sample container 2 in the manner of a sleeve in the region of the narrowing 3 and expands or compresses the sample container 2 in the radial and/or longitudinal direction upon electrical actuation. As a result, a shock wave is generated in the sample liquid located in the sample container 2, which shock wave is reflected at the narrowing 3 and leads to the microdroplets 8 being discharged from the nozzle 7.

Figure 5:
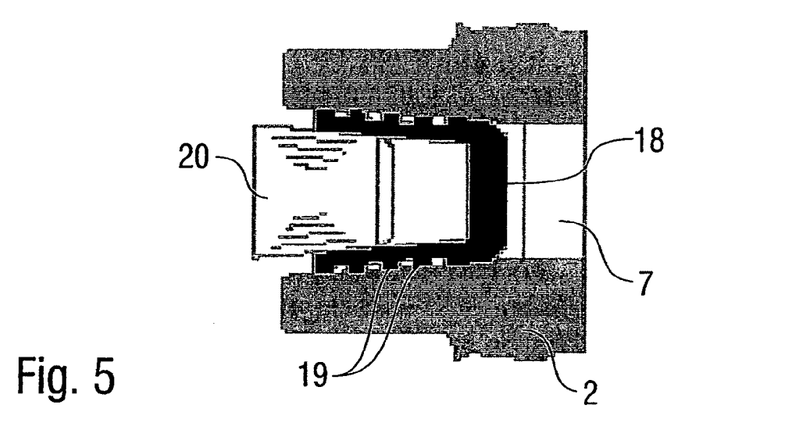
FIG. 5 shows a cross-sectional view of a stopper for closing the microdispenser according to the invention during transport and storage.

Of particular importance in this example of embodiment is the fact that the sample container 2 is completely closed apart from the nozzle 7 and cannot be refilled, so that the microdispenser 1 is designed for single use. The microdispenser 1 is therefore filled with a predefined sample liquid at the factory and then delivered in the filled state, so that contamination as a result of refilling operations is completely ruled out. During storage and transport, the nozzle 7 may additionally be closed by means of a stopper, a film or by means of wax, in order to hermetically seal the sample container 2. One example of embodiment of a stopper for closing the nozzle 7 is shown in FIG. 5 and will be described in more detail below.

Moreover, the microdispenser 1 has a barcode 10 which contains information about the microdispenser 1 (e.g. nozzle diameter, container volume) and the sample liquid located in the sample container 2, in coded form.

Figure 2:
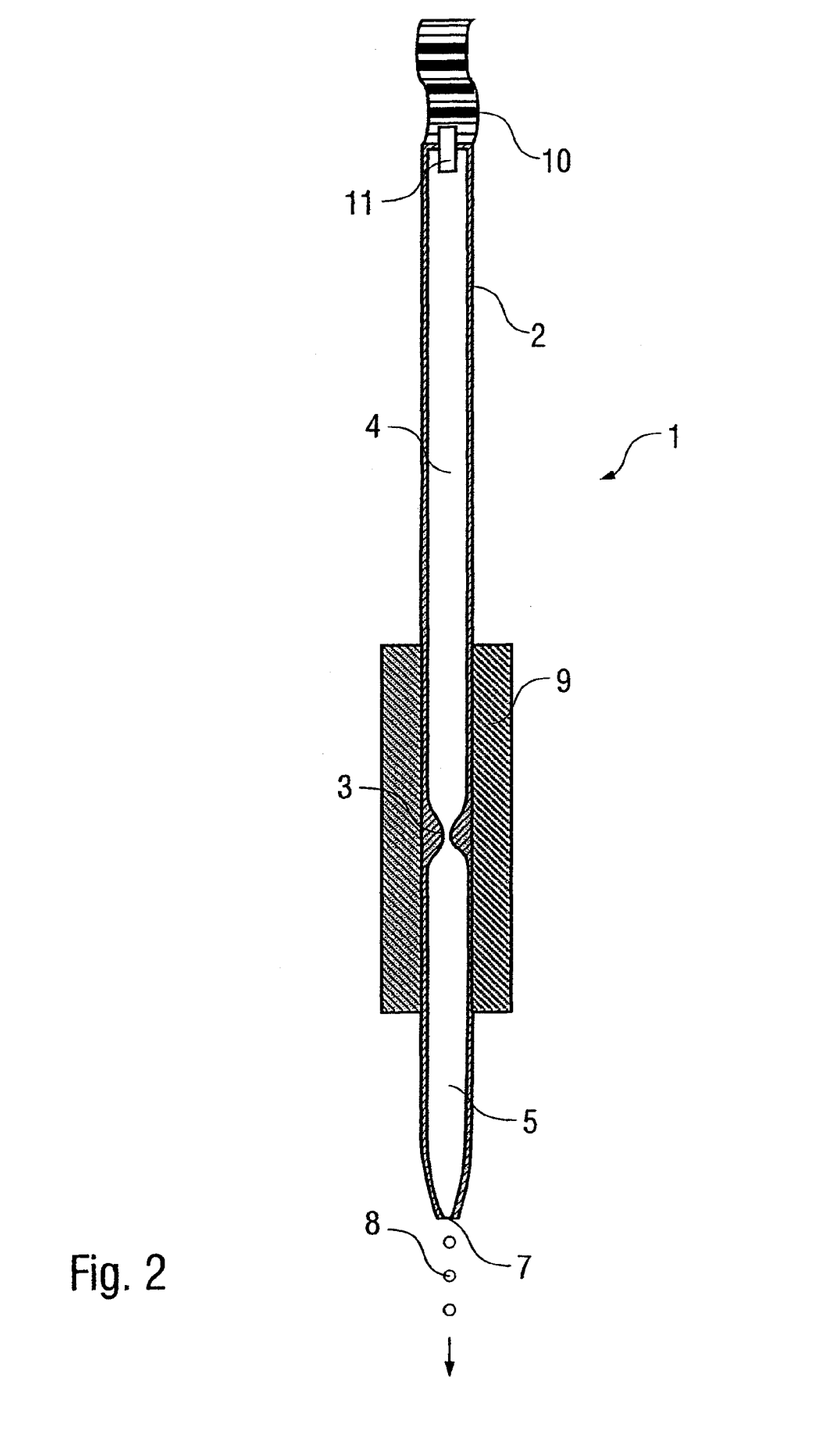
FIG. 2 shows a cross-sectional view of an alternative example of embodiment of a reusable microdispenser according to the invention, with a valve for venting and filling the microdispenser.

The alternative example of embodiment shown in FIG. 2 largely corresponds to the example of embodiment shown in FIG. 1 and described above, so that, in order to avoid repetition, reference will largely be made to the above description, wherein the same reference numerals are used for corresponding components and elements.

Figure 4A:
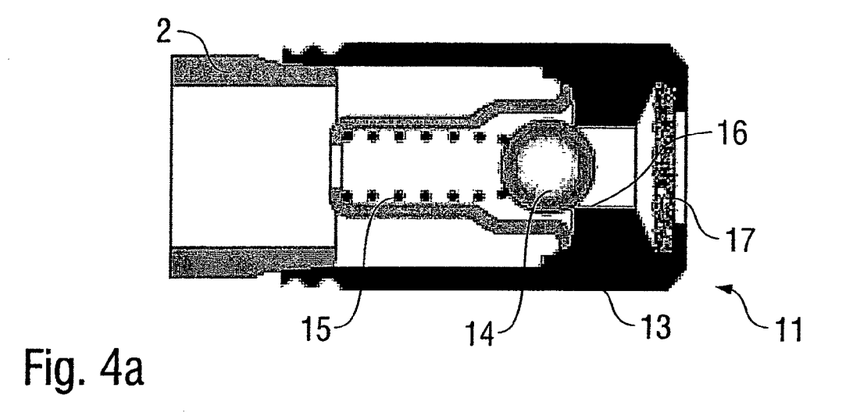
FIGS. 4a, 4b show different examples of embodiments of the valve for the microdispenser shown in FIG. 2.
Figure 4B:
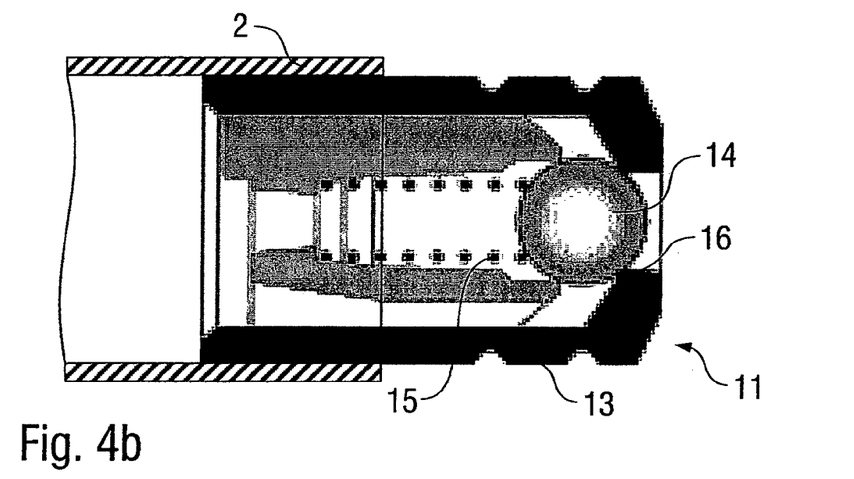

One special feature of this example of embodiment lies in the fact that the sample container 2 is not hermetically sealed but rather has a valve 11. The valve 11 on the one hand makes it possible to vent the sample container 2 during the dispensing operation, so that the dispensing of the microdroplets 8 is not prevented by the build-up of a vacuum within the sample container 2. The valve 11 also makes it possible to refill the sample container 2, which permits reuse of the microdispenser 1. However, the valve 11 is structurally integrated in the microdispenser and can be closed, so that no sample liquid can escape from the filled sample container 2 during transport and storage of the microdispenser 1. FIGS. 4a and 4b show different examples of embodiments of the valve 11, which will be described in more detail below.

Figure 3:
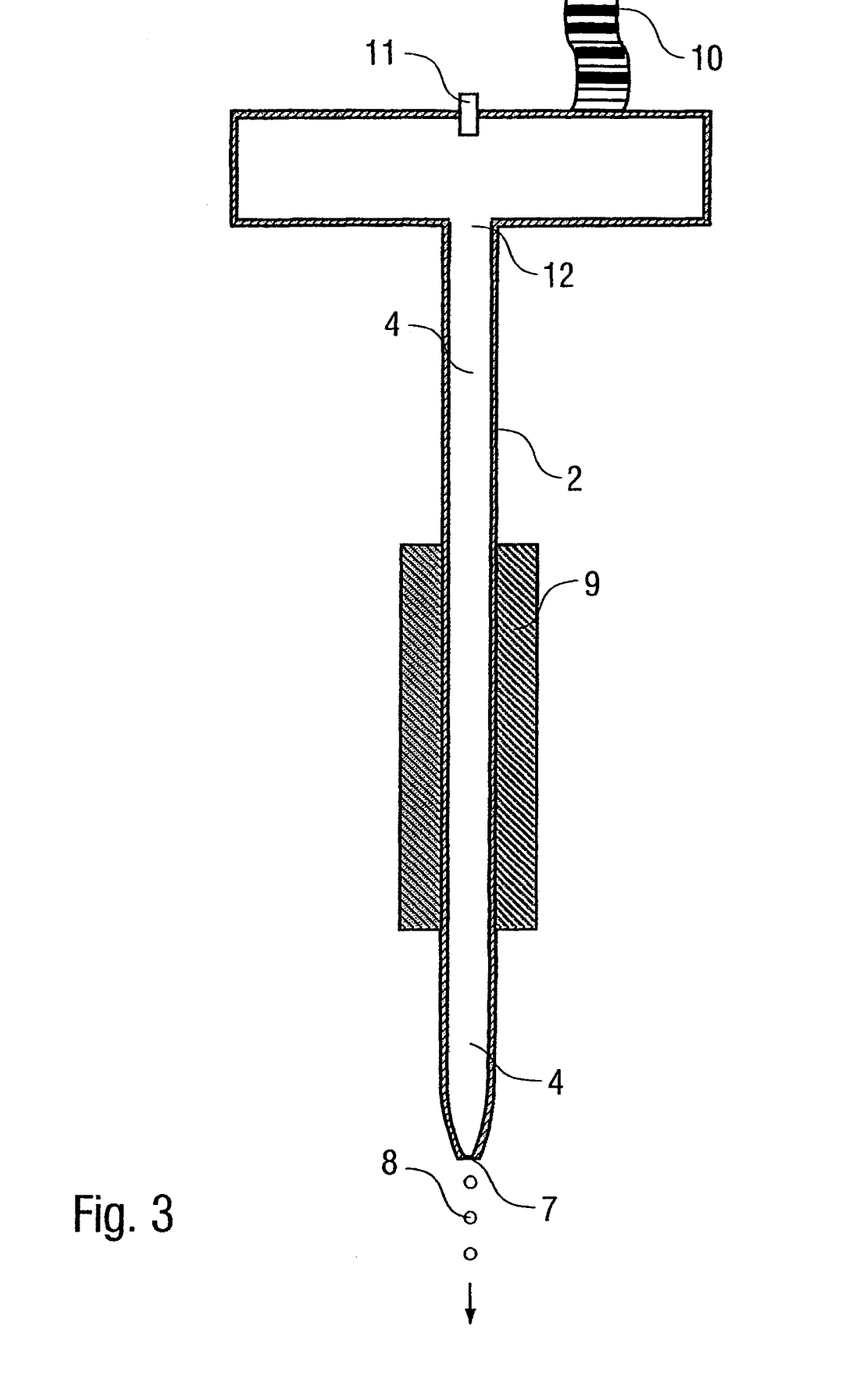
FIG. 3 shows a cross-sectional view of a further example of embodiment of a microdispenser according to the invention, with a widening of the cross section in order to reflect shock waves in the sample container.

FIG. 3 shows a further example of embodiment of a microdispenser 1 according to the invention, which once again largely corresponds to the examples of embodiments described above, so that, in order to avoid repetition, reference will largely be made to the above description, wherein the same reference numerals are used for corresponding components.

One special feature of this example of embodiment lies in the fact that the sample container 2 has, instead of the narrowing 3, a widening 12 of the cross section at which shock waves are likewise reflected, as explained in the aforementioned dissertation by Wolfgang Wehl: "Akustik und Fluidmechanik in Kanälen und Düsen von Tintenschreibwerken".

FIG. 4a shows a cross-sectional view of an example of embodiment of the valve 11 with a valve housing 13 made of plastic, which is shrunk onto the sample container 2 and then securely connected to the sample container 2 in a gas-tight manner. To this end, the valve housing 13, which has been slightly underdimensioned, is heated and then pushed onto the sample container 2 in the heated and therefore expanded state. During subsequent cooling to ambient temperature, the valve housing 13 then contracts again, which leads to a secure fit of the valve housing 13 on the sample container 2.

However, it is also possible as an alternative that the valve housing 13 is connected to the sample container 2 by means of an adhesive join.

In the valve housing 13, a valve ball 14 is pressed against a valve seat 16 by a coil spring 15. The valve 11 therefore opens only in one direction when the pressure difference acting from outside is large enough to lift the valve ball 14 away from the valve seat 16 counter to the force of the coil spring 15. Here, the prestress and the spring stiffness of the coil spring 15 are selected such that the valve 11 slowly opens when the piezo actuator 9 is actuated and as the sample container 2 becomes increasingly empty, so as to vent the sample container 2.

The valve 11 in this example of embodiment also has a screen 17 (or a membrane) which prevents foreign bodies from entering the sample container 2 during filling of the sample container 2.

FIG. 4b shows an alternative example of embodiment of the valve 11 which largely corresponds to the example of embodiment described above, so that, in order to avoid repetition, reference will largely be made to the above description in respect of FIG. 4a, wherein the same reference numerals are used for corresponding components.

One special feature of this example of embodiment lies in the fact that the sample container 2 is shrunk onto the valve housing 13 during assembly. To this end, the sample container 2, which has been slightly underdimensioned, is heated and then pushed onto the valve housing 13 in the heated and therefore expanded state. During subsequent cooling to ambient temperature, the sample container 2 then contracts again, which leads to a secure fit of the sample container 2 on the valve housing 13.

Finally, FIG. 5 shows a cross-sectional view of a stopper 18 which can be pressed into the nozzle 7 of the sample container 2 in order to prevent sample liquid from escaping from the sample container 2 during storage or transport. The stopper 18 is made of plastic and tapers slightly in a conical manner, which facilitates insertion of the stopper 18 into the nozzle 7. On its conical outer surface, the stopper 18 has a plurality of sealing ribs 19 running annularly, as a result of which the surface pressure between the stopper 18 and the inside of the nozzle 7 is increased and thus the sealing effect is improved.

Furthermore, the stopper 18 is designed in a pot-shaped manner and is open towards the outside, so that the stopper 18 can be pressed into the nozzle 7 by means of a ram 20.

Figure 6:
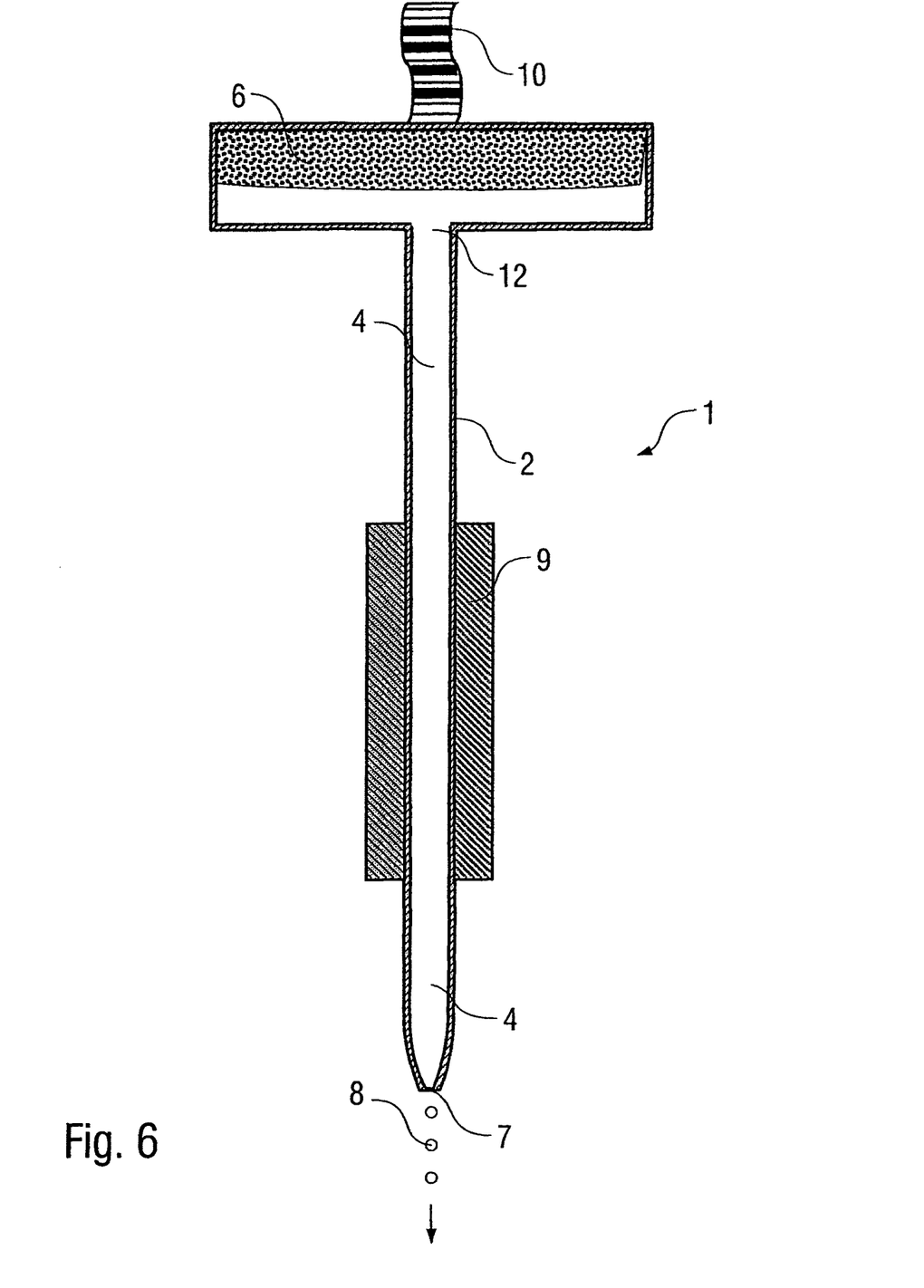
FIG. 6 shows a cross-sectional view of a further example of embodiment of a microdispenser according to the invention, without a valve but with a widening of the cross section.

The alternative example of embodiment shown in FIG. 6 largely corresponds to the examples of embodiments described above which are shown in FIG. 1 and FIG. 3, so that, in order to avoid repetition, reference will largely be made to the above description, wherein the same reference numerals are used for corresponding components and elements.

This example of embodiment combines the closed structure of the example of embodiment shown in FIG. 1 with the widening of the cross section in the example of embodiment shown in FIG. 3.

Figure 7A:
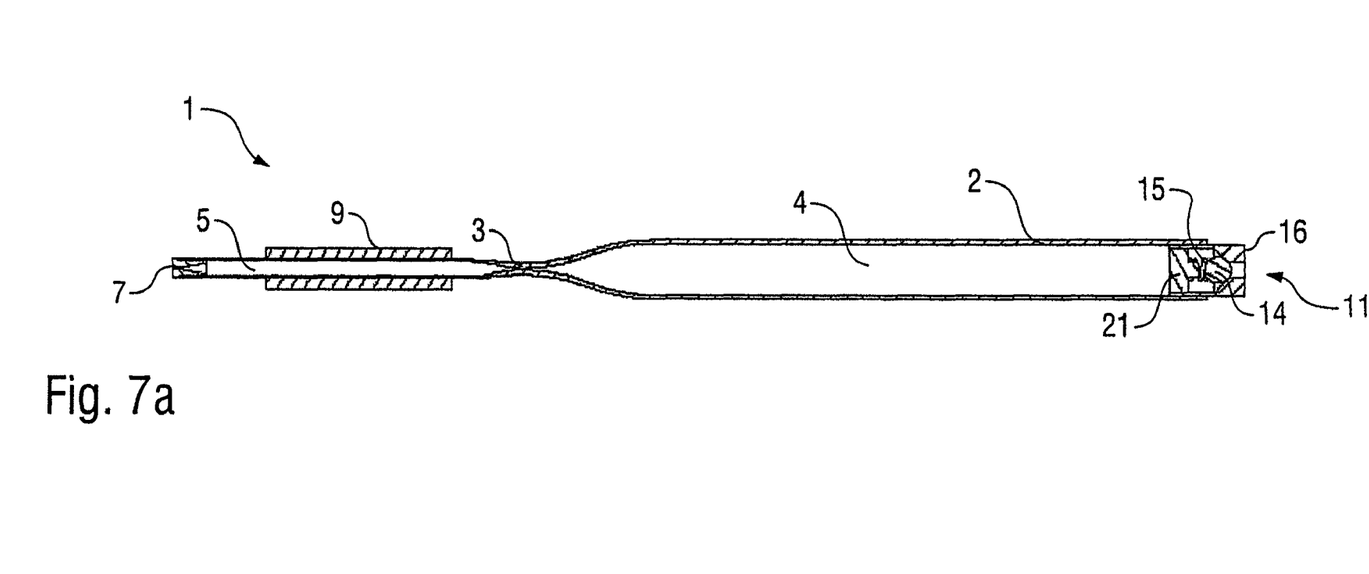
FIGS. 7a, 7b show a cross-sectional view and a side view, respectively, of a further example of embodiment of a microdispenser according to the invention, with an enlarged sample reservoir.
Figure 7B:
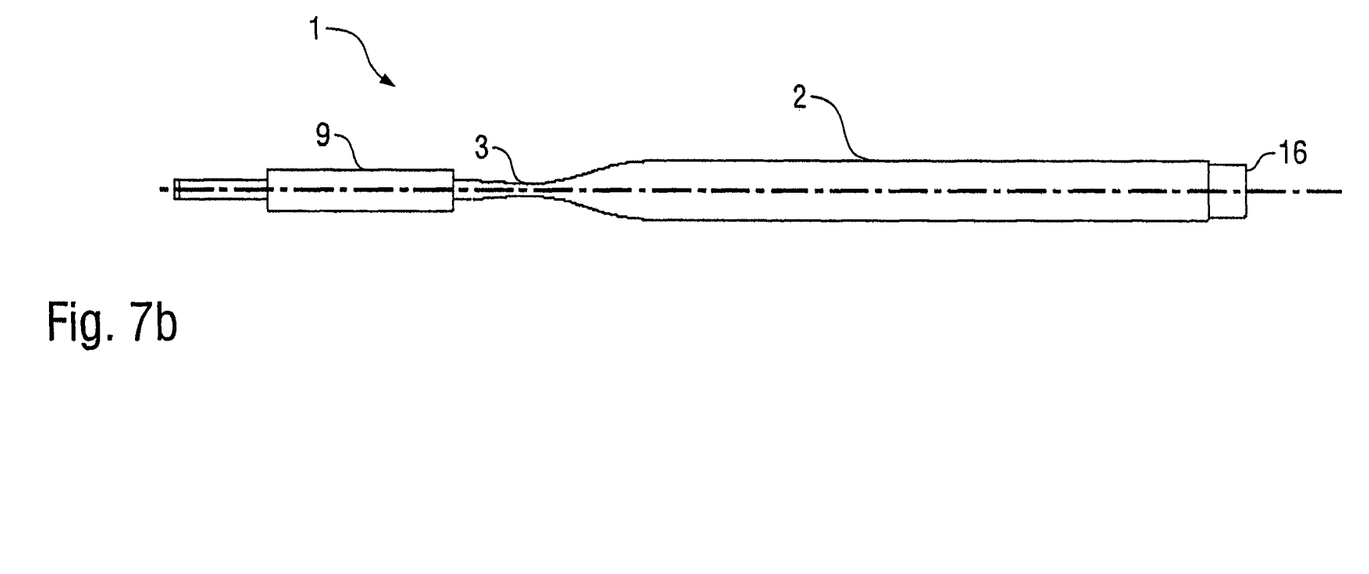
Figure 8A:
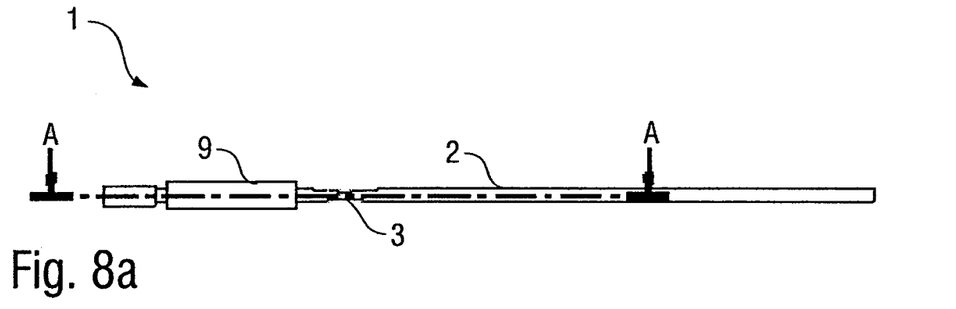
FIGS. 8a-8d show different views of a further example of embodiment of a microdispenser according to the invention, with a nozzle cap which forms the nozzle.
Figure 8B:
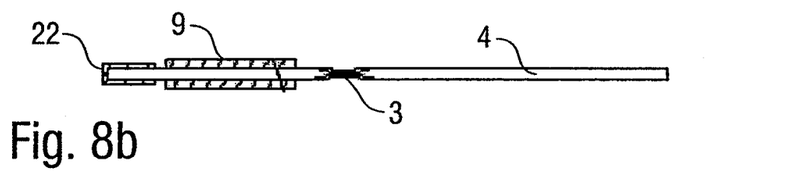
Figures 8C, 8D:
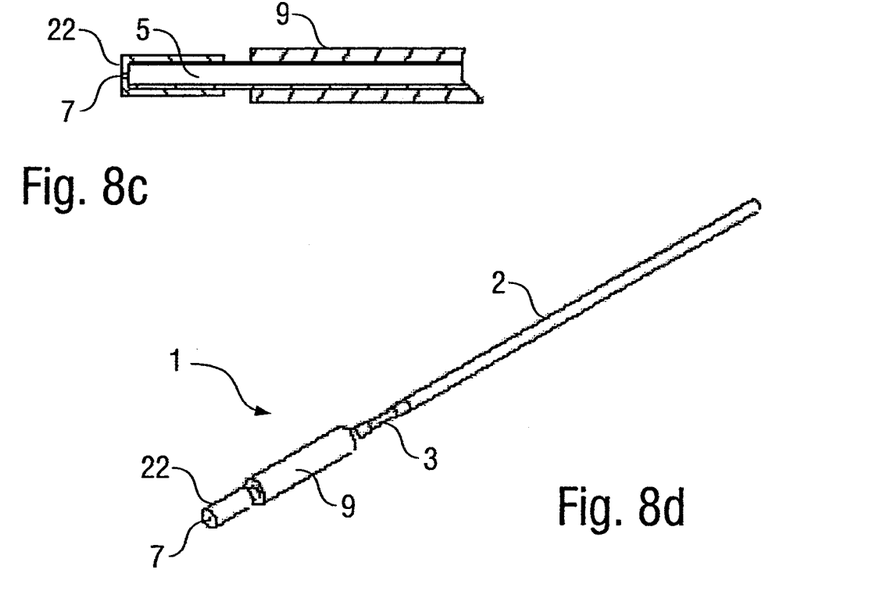

FIGS. 7a and 7b show a further example of embodiment of a microdispenser 1 according to the invention, which once again largely corresponds to the examples of embodiments described above, so that, in order to avoid repetition, reference will largely be made to the above description, wherein the same reference numerals are used for corresponding components.

One special feature of this example of embodiment lies in the fact that the sample reservoir 4 has a much larger diameter than the working chamber 5 of the sample container 2. Accordingly, the sample reservoir also has a larger volume than the working chamber 5. This offers the advantage that the microdispenser 1 can dispense a plurality of more than one million microdroplets 8 one after the other, without intermediate refilling of the microdispenser being necessary.

Another special feature of this example of embodiment lies in the fact that the nozzle 7 is formed by a nozzle stopper which is pressed into a corresponding opening in the working chamber 5. The nozzle geometry in this case is therefore not determined by the shape of the opening in the working chamber 5, which opens up a greater number of design options with regard to the nozzle geometry.

Furthermore, the microdispenser 1 in this example of embodiment has a particular design of the valve 11 comprising the valve ball 14, the valve seat 16 and a stopper 21, wherein the coil spring 15 is supported against the inside of the stopper 21 and the coil spring 15 pushes into the valve seat 16.

Furthermore, the piezo actuator 9 in this example of embodiment is entirely arranged in the region of the working chamber 5, i.e. on the nozzle side of the narrowing 3.

FIGS. 8a to 8d show a further example of embodiment of a microdispenser 1 according to the invention, which once again largely corresponds to the example of embodiment described above and shown in FIGS. 7a and 7b, so that, in order to avoid repetition, reference will largely be made to the above description, wherein the same reference numerals are used for corresponding components.

One special feature of this example of embodiment lies in the fact that the nozzle 7 is formed by a nozzle cap 22 which is pushed onto the front end of the working chamber 5 and has a nozzle opening in its end face. The nozzle geometry in this case is therefore not determined by the shape of the opening in the working chamber 5, which opens up a greater number of design options with regard to the nozzle geometry.

Figure 9A:
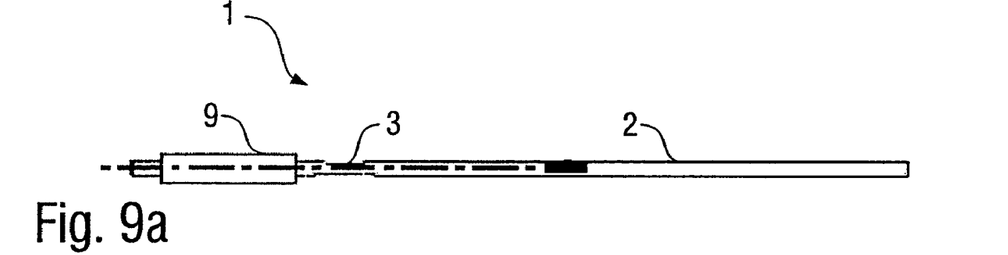
FIGS. 9a-9c show different views of a further example of embodiment of a microdispenser according to the invention, with a glued-on nozzle film which forms the nozzle.
Figure 9B:
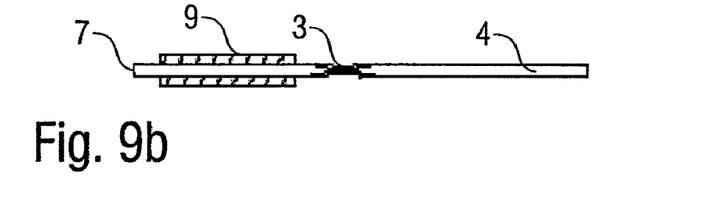
Figure 9C:
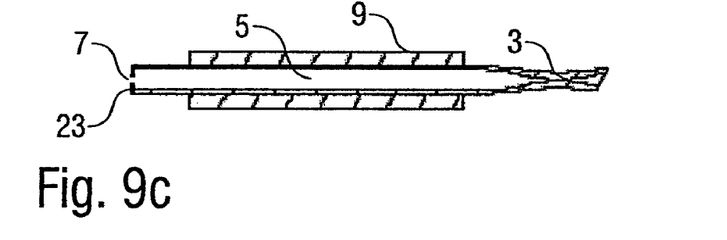
Figure 10A:
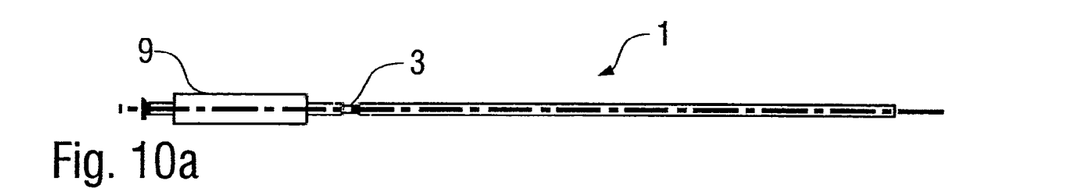
FIGS. 10a-10e show different views of a further example of embodiment of a microdispenser according to the invention, with a glued-on closure film which closes the nozzle during storage and transport.
Figures 10B, 10C, 10D:
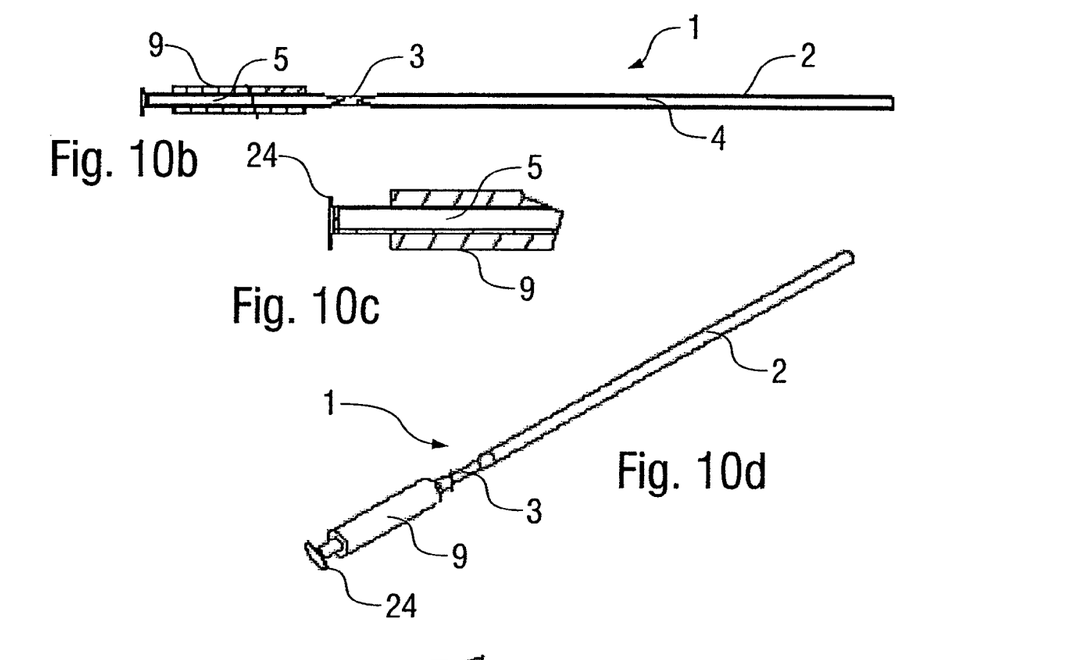
Figure 10E:
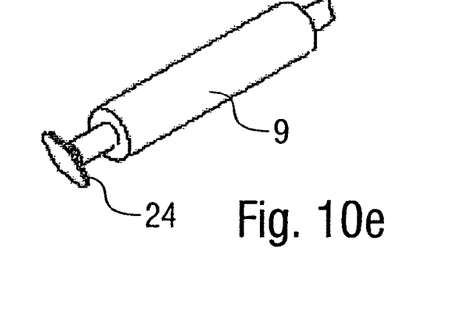

FIGS. 9a to 9c show a further example of embodiment of a microdispenser 1 according to the invention, which once again largely corresponds to the example of embodiment described above and shown in FIGS. 7a and 7b, so that, in order to avoid repetition, reference will largely be made to the above description, wherein the same reference numerals are used for corresponding components.

One special feature of this example of embodiment lies in the fact that the nozzle 7 is formed by a nozzle film 23 which is glued or welded onto the front end of the working chamber 5 and has a nozzle opening in its centre. The nozzle geometry in this case too is therefore not determined by the shape of the opening in the working chamber 5, which opens up a greater number of design options with regard to the nozzle geometry.

FIGS. 10a to 10e show a further example of embodiment of a microdispenser 1 according to the invention, which once again largely corresponds to the example of embodiment described above and shown in FIGS. 7a and 7b, so that, in order to avoid repetition, reference will largely be made to the above description, wherein the same reference numerals are used for corresponding components.

One special feature of this example of embodiment lies in the fact that the nozzle 7 is closed by a closure film 24, which prevents sample liquid from being able to escape from the sample container 2 through the nozzle 7 during storage and transport of the microdispenser. Prior to the dispensing operation, the closure film 24 is then simply pulled away from the nozzle 7, the removal of the closure film 24 from the nozzle 7 being facilitated by means of laterally protruding tabs.

Figure 11A:
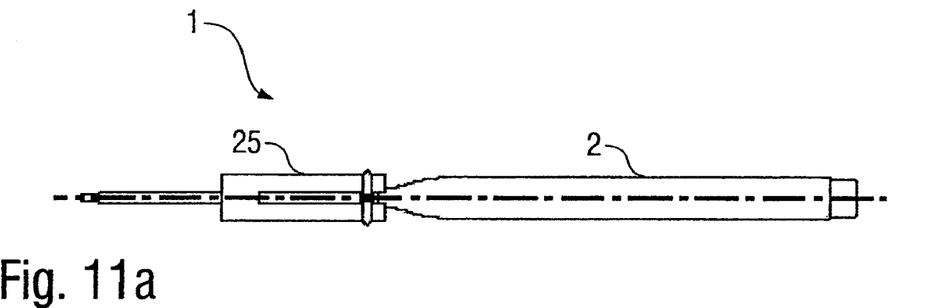
FIGS. 11a-11d show different views of a further example of embodiment of a microdispenser according to the invention with a pushed-on piezo actuator, which is secured by a mounting sleeve and a securing ring.
Figures 11B, 11C:
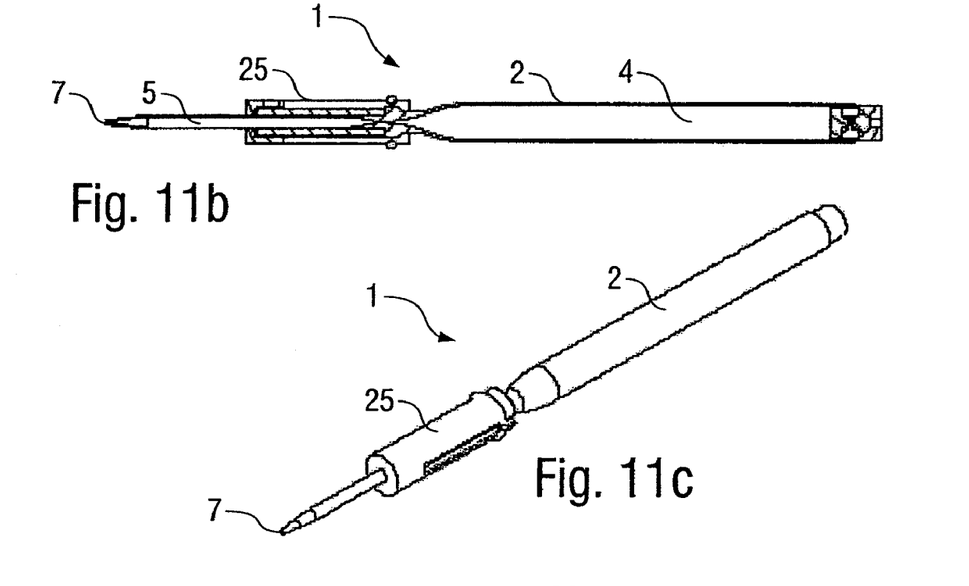
Figure 11D:
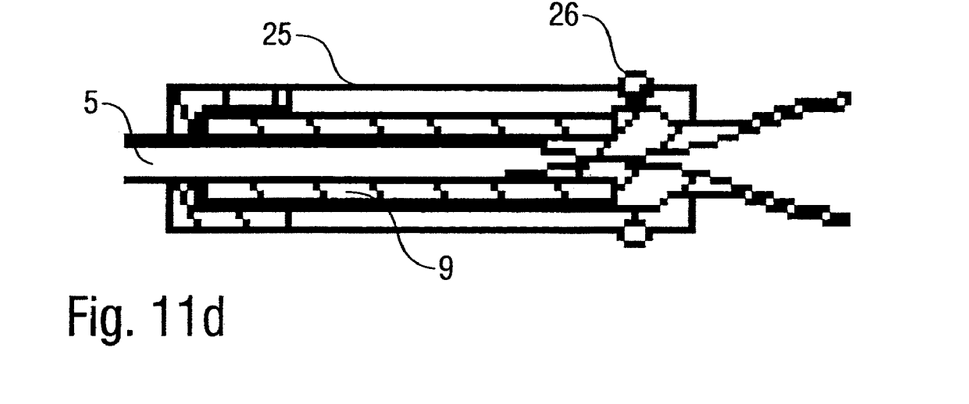

FIGS. 11a and 11c show a further example of embodiment of a microdispenser 1 according to the invention, which once again largely corresponds to the examples of embodiments described above, so that, in order to avoid repetition, reference will largely be made to the above description, wherein the same reference numerals are used for corresponding components.

One special feature of this example of embodiment lies in the fact that the piezo actuator 9 is pushed axially onto the sample container 2, wherein the piezo actuator 9 butts against an annular peripheral stop. In order to mechanically fix the piezo actuator 9 on the microdispenser 1, a mounting sleeve 25 is provided which is pushed onto the piezo actuator 9 in the axial direction and has on each side an axially running slot which facilitates a slight radial expansion of the mounting sleeve 25, as a result of which it is easier to push the mounting sleeve 25 on. Once the mounting sleeve 25 has been pushed on, the latter is mechanically fixed by means of a securing ring 26.

The invention is not restricted to the preferred examples of embodiments described above. Rather, a plurality of variants and modifications are possible which likewise make use of the inventive concept and which therefore fall within the scope of protection.

LIST OF REFERENCE NUMERALS

1 microdispenser
2 sample container
3 narrowing
4 sample reservoir
5 working chamber
6 sponge
7 nozzle
8 microdroplets
9 piezo actuator
10 barcode
11 valve
12 widening of cross section
13 valve housing
14 valve ball
15 coil spring
16 valve seat
17 screen
18 stopper
19 sealing ribs
20 ram
21 stopper
22 nozzle cap
23 nozzle film
24 closure film
25 mounting sleeve
26 securing ring

The invention claimed is:

1. A microdispenser for dispensing a liquid sample in a dispensing device, comprising
   a) a sample container for holding the liquid sample,
   b) a nozzle for dispensing the sample located in the sample container, wherein the nozzle is adapted to dispense the liquid sample in a form of microdroplets,
   c) an actuator for discharging the liquid sample located in the sample container through the nozzle, wherein the actuator is a piezo actuator,
   d) a closure adapted for closing the nozzle for storage of the microdispenser and adapted for opening the nozzle for dispensing the sample liquid,
   e) a valve for venting the sample container during the dispensing of the liquid sample, a marking containing information about the microdispenser or about the liquid sample located in the sample container, said marking being an optical code, and
   g) a sponge arranged in the sample container such that the sponge is adapted to generate a holding vacuum in the sample container due to capillary forces acting on the liquid sample,
wherein: (i) the microdispenser with the sample container containing the liquid sample can be stored independently of and fluidically separated from the dispensing device, without the sample escaping from the sample container during storage, (ii) the sample container has an integrated sample reservoir in order to be able to dispense a plurality of samples one after the other without a need for refilling, (iii) no sample supply line for the microdispenser is provided, (iv) the nozzle is provided with a coating, and (v) the coating has an effect selected from the group consisting of protein-immobilization, DNA-immobilization, permission of specific adsorption of biomolecules, prevention of coagulation of the liquid sample, purification of the liquid sample and concentrating of the liquid sample.

2. The microdispenser according to claim 1, wherein the microdispenser is configured for a single use, and the sample container is not refillable.

3. The microdispenser according to claim 1, wherein the sample container is completely closed apart from the nozzle and has no opening apart from the nozzle.

4. The microdispenser according to claim 1, further comprising a valve for filling the sample container.

5. The microdispenser according to claim 1, further comprising a shrink fit material connecting the valve to the sample container.

6. The microdispenser according to claim 1, further comprising an adhesive connecting, wherein the valve to the sample container.

7. The microdispenser according to claim 1, wherein an inside of the sample container has a stepped cross-section.

8. The microdispenser according to claim 7, wherein the stepped cross-section is a narrowing of the cross-section.

9. The microdispenser according to claim 7, wherein the stepped cross-section is a widening of the cross-section.

10. The microdispenser according to claim 1, wherein the sample container is made of a material selected from the group consisting of plastic, glass and ceramic.

11. The microdispenser according to claim 1, wherein the nozzle is made of a material selected from the group consisting of plastic, glass and ceramic.

12. The microdispenser according to claim 1, wherein the actuator is structurally integrated in the microdispenser.

13. The microdispenser according to claim 1, wherein the actuator is structurally separate from the microdispenser.

14. The microdispenser according to claim 1, further comprising a material fit connection of the actuator and the sample container.

15. The microdispenser according to claim 1, further comprising a friction fit connection of the actuator and the sample container.

16. The microdispenser according to claim 1, further comprising a form fit connection of the actuator and the sample container.

17. The microdispenser according to claim 1, wherein the actuator surrounds the outside of the sample container as a sleeve and compresses and expands the sample container upon electrical actuation of the actuator.

18. The microdispenser according to claim 1, wherein the actuator is fixed on the sample container by way of a mounting sleeve.

19. The microdispenser according to claim 18, wherein the mounting sleeve has a spring slot, which runs in an axial direction.

20. The microdispenser according to claim 18, wherein the mounting sleeve is fixed on the sample container by screwing.

21. The microdispenser according to claim 18, wherein the mounting sleeve is fixed on the sample container by means of a securing ring.

22. The microdispenser according to claim 1, wherein the closure is a member selected from the group consisting of a stopper, a closure film, a wax and a closure cap.

23. The microdispenser according to claim 1, wherein the sample container has a volume in a range from 1 nl to 1 ml.

24. The microdispenser according to claim 1, wherein the nozzle has a nozzle diameter in a range from 10 μM to 100 μm.

25. The microdispenser according to claim 1, wherein the sample container has a working chamber in addition to the sample reservoir, wherein the sample reservoir has a larger volume than the working chamber.

26. An operating method for a microdispenser according to claim 1, said method comprising the following steps:
   (a) closing the nozzle prior to storage of the microdispenser;
   (b) storing the microdispenser comprising the sample container containing the liquid sample separately from the dispensing device;
   (c) reading information about the microdispenser or about the sample located in the sample container from the optical code;
   (d) opening the nozzle after storage and before dispensing the sample;
   (e) dispensing the liquid sample in the form of microdroplets; and
   (f) venting the sample container through a valve during the dispensing step.

27. The operating method according to claim 26, wherein the sample container is not refilled and the microdispenser is disposed of after at least one dispensing operation.

28. The operating method according to claim 26, wherein:
   the information is read from the marking during storage of the microdispenser, and
   the microdispenser is removed from storage or remains in storage depending on the information that is read.

29. The operating method according to claim 26, wherein the microdispenser is returned to storage after a dispensing operation.

30. The operating method according to claim 26, wherein the sample container is filled with the liquid sample through the nozzle by capillary action.

31. The operating method according to claim 26, wherein the sample container is filled with the liquid sample through a valve.

32. The operating method according to claim 26, wherein concentration of the sample is provided by way of the coating of the nozzle and of the sample container.

* * * * *